US005698215A

United States Patent [19]

Kalili et al.

[11] Patent Number: 5,698,215
[45] Date of Patent: Dec. 16, 1997

[54] CHEWING GUM COMPOSITION WITH FLUORIDE AND CITRIC ACID

[76] Inventors: Tom Kalili, 10390 Wilshire Blvd. #510, Los Angeles, Calif. 90024; Angelo A. Caputo, 26323 W. Bravo La., Calabasas, Calif. 91302

[21] Appl. No.: 768,886

[22] Filed: Dec. 17, 1996

Related U.S. Application Data

[63] Continuation of Ser. No. 451,397, May 26, 1995, Pat. No. 5,585,110, which is a continuation of Ser. No. 218,434, Mar. 28, 1994, abandoned.

[51] Int. Cl.$^6$ ........................................... A61K 9/68
[52] U.S. Cl. ........................ 424/440; 424/48; 424/49; 424/52
[58] Field of Search ..................... 424/440, 48, 49, 424/52; 426/5

[56] References Cited

U.S. PATENT DOCUMENTS

| | | | |
|---|---|---|---|
| 4,233,288 | 11/1980 | Cornell | 424/48 |
| 4,474,749 | 10/1984 | Kruppa | 424/48 |
| 4,563,345 | 1/1986 | Arrick | 424/48 |
| 5,017,385 | 5/1991 | Wienecke | 426/5 |

*Primary Examiner*—Thurman K. Page
*Assistant Examiner*—Sharon Howard
*Attorney, Agent, or Firm*—Burns, Doane, Swecker and Mathis

[57] ABSTRACT

This patent deals with a chewing gum which possesses fluoride and citric acid for improved dental health. The incorporation of fluoride and citric acid into our gum product is for the citric acid to provide a means by which fluoride can be absorbed into the tooth structure. The mechanism of action of this product is the following: citric acid is incorporated in this chewing gum to microscopically open up the pores (prism layers) of the enamel tooth structure. This opening of the pores, at the moth surface, enables greater contact and penetration of the fluoride to be absorbed into the enamel. The resultant effect is greater penetration of fluoride into the enamel and the underlying tooth structure (dentine). In addition to facilitating the penetration of fluoride into the tooth, there would be an added benefit from the dietary content of the citrus fruits. Moreover, this gum includes novel organoleptic properties as a result of natural sugars, together with enhanced flavor, for sweetness impact.

20 Claims, No Drawings

CHEWING GUM COMPOSITION WITH FLUORIDE AND CITRIC ACID

This is a continuations of U.S. patent application Ser. No. 08/451,397, filed May 26, 1995, which issued as U.S. Pat. No. 5,585,110 on Dec. 17, 1996, which was a continuation of U.S. application Serial No. 08/218,434, filed on Mar. 28, 1994, now abandoned.

FIELD OF INVENTION

The present invention relates to a chewing gum with organoleptic properties which possesses fluoride and citric acid for improved dental health.

BACKGROUND OF THE INVENTION

Fluoride compounds have been incorporated into dental topicals and into consumables for the prevention of tooth decay. This prevention is by virtue of such effects as strengthening of the enamel, suppression of the enzymatic action of bacteria which convert saccharids into acids and suppression of the propagation of microorganisms relating to the corrosion destruction of enamel and dentine. Studies have demonstrated that fluoride combines with hydroxyapatite, the crystalline structure of the teeth, to produce a modified crystalline structure which is more resistant to acid attack.

A wide variety of fluorides have been disclosed in the prior art, including sodium fluoride, indium fluoride, sodium monofluorophosphate, stannous fluoride, fluoroalkyl phosphates, and quaternary ammonium fluorides. These and other fluorides have been incorporated into gels, rinses, toothpastes, tooth powder, chewing gum and the like for topical application. Fluoride treatment can also be undertaken through consumables, fluoridated drinking water and fluoride tablets. It has been definitely established, on the basis of large studies in a number of communities that the fluoridation of water to a concentration of 1.0 ppm is a safe and practical public health measure. The resultant effect is 50-66% reduction in the incidents of dental carries in permanent teeth. It has also been demonstrated, in a 15 year study, that the administration of sodium fluoride in relatively small amounts during pregnancy resulted in almost complete elimination of dental carries in subsequently born children. (Glenn, Journal of Dentistry for Children, January 1980.)

Numerous patents have been issued which describe chewing gum with fluoride-containing salts: Arrick, et al. U.S. Pat. No. 4,563,345; Robyt et al. U.S. Pat. No. 4,228,150; Terra et al. U.S. Pat. No. 4,265,877; Goupil U.S. Pat. No. 4,284,650; Cornell U.S. Pat. No. 4,233,288; Bilotti et al. U.S. Pat. No. 3,075,884; Merckel et al. U.S. Pat. No. 2,627,493; and Merckel et al. U.S. Pat. No. 2,700,012. Each of these inventions have an improvement over the prior art, and each incorporate fluorides in different forms into chewing gums.

The ingestion of any significant mount of fluoride (as low as one gram of sodium fluoride) can produce consequences such as abdominal cramping and possible vomiting. As noted by U.S. Pat. No. 5,071,637 issued to Pellico, et al., the risk is noteworthy in flavored fluoride products which can be unintentionally swallowed in significant mounts. Therefore, the mount of fluoride used in a chewing gum is limited, yet effective.

However, the need for a composition which facilitates the optimal uptake of fluoride by teeth is apparent and has not been fulfilled by the prior art.

SUMMARY OF THE INVENTION

The chewing gum of the present invention relates to a chewing gum that has a novel mechanism whereby fluoride is incorporated into the prism layers (pores) of the enamel tooth structure.

The chewing gum of the present invention incorporates the biochemical reaction which momentarily takes place following the exposure of dental enamel to citric acid at the microscopic level. This reaction is a natural occurrence which results multiple times on a daily basis each and every time one ingests any of the citrus fruits in the market. This pore opening is the pathway for fluoride, which is within the gum product, to penetrate into the prismatic layers of the tooth structure. Hence, there is a greater surface exposure of the fluoride with the dental enamel. The specific fruits which are primarily citric acid in nature are: oranges, grapefruits, lemons, limes, tangerines, and the like.

The combination of such a citric acid with fluoride creates a momentary micro-atmosphere for a pathway which enables the fluoride to ingress into the prism layers of the enamel. This mechanism in a chewing gum having organoleptic properties, would produce an enhanced flavor and sweetness impact which would make this product a standout for both taste and optimum dental health. As a result, the product includes a natural high impact aromatic flavor from these fresh and biocompatible agents.

The fundamental principle of utilizing the citrus type of fruits therefore becomes two-fold: (a) to establish a natural citrus fruit taste which is an enjoyable taste to the general public, and (b) to provide the mechanism of chemical reaction which takes place when the citric acid of the citrus fruits comes into contact with the enamel tooth structure. These benefits would be achieved in the absence of artificial, synthetic ingredients such as, artificial sweeteners, saccharin salts, sodium or calcium saccharin salts, cyclamate salts, such as the sodium salt, and the like, and the free acid form of saccharin. Such ingredients are common in most chewing gum products in the market today.

DETAILED DESCRIPTION OF THE INVENTION

The composition of this invention comprises a chewing gum base, citric acid derived from fruits, flavoring, and an oral health agent.

The chewing gum composition generally comprises one or more natural or synthetic elastomers and can be supplemented by conventional chewing gum ingredients. These ingredients include one or more solvents, plasticizers, fillers, flavoring agents, coloring agents and/or sweetening agents. Elastomers which are suitable for use herein include substances of vegetable origin such as chicle, jelutong, gutta percha, guayule, and crown gum.

Synthetic elastomers such as butadiene-styrene copolymers, isobutylene-isoprene copolymers, polyethylene, polyisobutylene, polyvinylacetate, and mixtures thereof are also useful. The elastomer generally comprises from about 14% to 50% by weight (preferably from about 20% to about 30% by weight) of the chewing gum composition.

The chewing gum composition can contain elastomer solvents to aid in softening the polymer component. Such elastomer solvents can include methyl, glycerol or pentaerythritol esters of rosins or modified rosins, such as hydrogenated, dimerized or polymerized rosins or mixtures thereof. Examples of elastomer solvents suitable for use herein include pentaerythritol ester of partially hydrogenated, dimerized or polymerized rosins or mixtures thereof. Examples of elastomer solvents suitable for use herein include pentaerythritol ester of partially hydrogenated wood rosin, pentaerythritol ester of wood rosin, glycerol ester of partially dimerized rosin, glycerol ester of polymerized rosin, glycerol ester of tall oil rosin, glycerol ester of wood rosin, and partially hydrogenated wood rosin, and partially hydrogenated methyl ester of rosin, and mixtures thereof. Terpene resins, including polyterpene and mixtures thereof are also useful. The solvent can be employed in an amount ranging from about 10% to about 75% and preferably about 15% to about 50% by weight of the chewing gum composition.

A variety of traditional ingredients used as plasticizers, softeners or emulsifiers such as lanolin, lecithin, glyceryl monostearate, stearic acid, sodium stearate, potassium stearate, glyceryl triacetate, triacetin, glycerin, and the like as well as natural waxes, petroleum waxes, paraffin waxes, and microcrystalline waxes, can also be incorporated into the chewing gum composition to obtain a variety of desirable textures and consistency properties. These additional materials are generally employed in mounts of up to about 30% by weight, preferably about 1% to about 25% by weight and more preferably from about 3% to about 7% by weight of the final chewing gum composition. The chewing gum composition can additionally include conventional coloring agents such as titanium dioxide, and fillers such as dicalcium phosphate, aluminum hydroxide, alumina, aluminum silicates, talc, calcium carbonate, cellulose, and combinations thereof.

The flavoring compositions are natural sugars consisting of citrus type fruits for elicitation of natural sweet flavors such as lemons, limes, tangerines, grapefruits, and oranges. All contain natural sugars in the fructose group of sugars. The sugar groups are sugar alcohols which include sorbitol mannitol, xylitol, maltitol, and hydrogenated starch and glucose syrups produced by catalytic hydrogenation of carbohydrate syrups to the point where all carbohydrate end groups are reduced to alcohols. A suitable hydrogenated starch hydrolysate includes from about 6% to 10% sorbitol, from about 25% to about 55% maltitol and from 20% to about 40% hydrogenated higher saccharides. A typical hydrogenated starch hydrolysate is Lycasin (RTM). The amount of flavoring agents and/or flavor enhancers employed is normally a matter of preference, subject to such factors as flavor type, base type, and strength desired. In general, amounts of about 0.05% to about 3.0% by weight of the final composition are usable with amounts of about 0.3% to about 1.5% being preferred and about 0.7% to about 1.2% being more preferred.

The oral health agent takes the form of a fluoride which is added in levels of from about 0.001% to about 1% by weight for anti-caries purposes. It is a feature of the present invention which can provide substantially improved release of fluoride in comparison with that provided by conventional fluoride chewing gum products. Preferred fluorides are sodium fluoride, stannous fluoride, indium fluoride, sodium monofluorophosphate, fluoroalkyl phosphates, and quaternary ammonium fluorides.

The invention is illustrated by the following non-limiting examples:

EXAMPLE 1

A composition is prepared having the following
Gum base 57.5
Xylitol (60%) 6.7
Xylitol powder 30.0
Glycerol 4.0
Peppermint oil 0.8
Citrus Fruits 0.7–1.2
Fluoride 0.01%

In the above, the gum base consists of styrene butadiene elastomer, polyvinylacetate resin, a rosin ester, microcrystalline wax, and calcium carbonate. The chewing gum composition is prepared by warming the gum base to about 50 C. in a kneader, adding the glycerol, xylitol solution, and peppermint oil, all prewarmed to about 50° C., to the kneader, adding the xylitol powder and mixing until a homogeneous mass is achieved.

What is claimed is:

1. A composition for enhanced absorption of fluoride by teeth, the composition comprising:
   a chewing gum base;
   a fluoride compound; and
   an effective amount of citric acid to thereby enhance the penetration of fluoride into the teeth.

2. The composition of claim 1, wherein the chewing gum base is a synthetic elastomer.

3. The composition of claim 2, wherein the synthetic elastomer is selected from the group consisting of: butadiene-styrene copolymers, isobutylene-isoprene copolymers, polyethylene, polyisobutylene, polyvinylacetate, and mixtures thereof.

4. The composition of claim 1, wherein the chewing gum base is a vegetable-derived elastomer.

5. The composition of claim 4, wherein the vegetable-derived elastomer is selected from the group consisting of: chicle, jelutong, gutta percha, guayule, and crown gum.

6. The composition of claim 1, wherein the citric acid is supplied in the form of an additive derived from a citrus fruit selected from the group consisting of: oranges, grapefruits, lemons, limes, and tangerines.

7. The composition of claim 1, wherein the fluoride compound is selected from the group consisting of: sodium fluoride, sodium monofluorophosphate, stannous fluoride, indium fluoride, fluoroalkyl phosphate salt, quaternary ammonium fluoride, and mixtures thereof.

8. The composition of claim 1, further comprising:
   a sweetener.

9. The composition of claim 8, wherein the sweetener is selected from the group consisting of: natural sugars, citrus fruit sugar, saccharine, fructose, sorbitol, mannitol, xylitol, maltitol, hydrogenated starch, hydrolysate, hydrogenated higher saccharides, Lycasine (RTM), glucose, glucose syrups, and hydrogenated carbohydrate syrups.

10. The composition of claim 1, further comprising:
    a softening agent.

11. The composition of claim 10, wherein the softening agent is selected from the group consisting of: lanolin, lecithin, glyceryl monostearate, stearic acid, sodium stearate, potassium stearate, glyceryl triacetate, triacetin, glycerin, and the like as well as natural waxes, petroleum waxes, paraffin waxes, and microcrystalline waxes.

12. The composition of claim 1, further comprising:
    a solvent.

13. The composition of claim 12, wherein the solvent is selected from the group consisting of: methyl, glycerol, pentaerythritol esters of rosins, pentaerythritol esters of hydrogenated rosins, pentaerythritol esters of dimerized rosins, pentaerythritol esters of polymerized rosins, pentaerythritol ester of partially hydrogenated rosins, pentaerythritol ester of dimerized rosins, pentaerythritol ester of polymerized rosins, pentaerythritol ester of partially hydrogenated wood rosin, pentaerythritol ester of wood rosin, glycerol ester of partially dimerized rosin, glycerol ester of polymerized rosin, glycerol ester of tall oil rosin, glycerol ester of wood rosin, glycerol ester of partially hydrogenated wood rosin, partially hydrogenated methyl ester of rosin, terpene resins, polyterpene, and mixtures thereof.

14. The composition of claim 1, further comprising:
an emulsifier.

15. The composition of claim 14, wherein the emulsifier is selected from the group consisting of: lanolin, lecithin, glyceryl monostearate, stearic acid, sodium stearate, potassium stearate, glyceryl triacetate, triacetin, glycerin, natural waxes, petroleum waxes, paraffin waxes, and microcrystalline waxes.

16. The composition of claim 1, further comprising:
a filler.

17. The composition of claim 16, wherein the filler is selected from the group consisting of: dicalcium phosphate, aluminum hydroxide, alumina, aluminum silicates, talc, calcium carbonate, cellulose, and mixtures thereof.

18. The composition of claim 1, further comprising:
a flavoring agent.

19. The composition of claim 18, wherein the flavoring agent is peppermint oil.

20. A chewing gum composition comprising:

a chewing gum base;

a fluoride compound;

an effective amount of citric acid to enhance penetration of fluoride into teeth;

a softening agent; and a sweetener.

* * * * *